US005254328A

United States Patent [19]

Herscheid et al.

[11] Patent Number: 5,254,328

[45] Date of Patent: Oct. 19, 1993

[54] METHOD OF PREPARING A RADIODIAGNOSTIC COMPRISING A GASEOUS RADIONUCLIDE, AS WELL AS A RADIONUCLIDE GENERATOR SUITABLE FOR USING SAID METHOD

[75] Inventors: Jacobus D. M. Herscheid, Nieuw Vennep; Leo F. Van Rooij, Amstelveen, both of Netherlands

[73] Assignee: Mallinckrodt Medical, Inc., St. Louis, Mo.

[21] Appl. No.: 809,559

[22] PCT Filed: Jul. 11, 1990

[86] PCT No.: PCT/US90/03897

§ 371 Date: Jan. 23, 1992

§ 102(e) Date: Jan. 23, 1992

[30] Foreign Application Priority Data

Jul. 12, 1989 [NL] Netherlands ........................ 8901792

[51] Int. Cl.[5] ...................... A61K 43/00; C01G 57/00

[52] U.S. Cl. ........................................ 424/1.1; 423/2; 250/432 PD

[58] Field of Search ..................... 424/1.1; 423/249, 2; 250/423 R, 424, 496.1, 432 PD; 252/644, 645

[56] References Cited

U.S. PATENT DOCUMENTS

| | | | |
|---|---|---|---|
| 3,446,965 | 5/1969 | Ogier et al. | 250/428 |
| 3,740,558 | 2/1971 | Kato et al. | 250/106 T |
| 3,774,036 | 11/1973 | Gerhart | 250/106 T |
| 3,902,849 | 9/1975 | Barak et al. | 23/252 R |
| 4,876,076 | 10/1989 | Issachar et al. | 423/2 |

*Primary Examiner*—Robert L. Stoll
*Assistant Examiner*—Matthew Zmurko
*Attorney, Agent, or Firm*—Madson & Metcalf

[57] ABSTRACT

The invention relates to a method of preparing a radiodiagnostic comprising a gaseous radionuclide formed by radioactive decay of a parent nuclide, by eluting with a suitable eluent the radioactive daughter nuclide from the parent nuclide provided ionically on a carrier, by using as a carrier for the parent nuclide ions a membrane, in particular an ion exchange membrane, past which the eluent is made to flow.

The invention further relates to a radionuclide generator suitable for using said method.

11 Claims, 4 Drawing Sheets

METHOD OF PREPARING A RADIODIAGNOSTIC COMPRISING A GASEOUS RADIONUCLIDE, AS WELL AS A RADIONUCLIDE GENERATOR SUITABLE FOR USING SAID METHOD

The invention relates to a method of preparing a radiodiagnostic comprising a gaseous radionuclide formed by radioactive decay of a parent nuclide, by eluting with a suitable eluent the radioactive daughter nuclide from the parent nuclide provided ionically on a carrier.

Such radiodiagnostics are intended in particular for lung function examination and regional blood circulation measurements. Examples of gaseous radionuclides are radioactive noble gases which can be eluted inter alia with gaseous eluents, for example, oxygen or air, and are then suitable for pulmonary ventilation studies. For example, in combination with lung perfusion scintigraphy, lung defects, like pulmonary embolies, obstructions in the bronchi and the like, can in this manner be detected and localised in a simple manner.

A radioactive noble gas to be considered for such an examination is radioactive krypton, in particular krypton-81m ($^{81m}$Kr). Krypton-81m which has been available for a few years already, has favourable radiation characteristics, for example, a half life of only 13 seconds and the absence of beta rays. Due to the many favourable properties of krypton-81m, physical and chemical as well as physiological, there is hence an increasing interest for the use of this radionuclide in radiodiagnostics, in particular for pulmonary ventilation studies and regional blood circulation measurements. However, krypton-81m may also be used for example for lung perfusion scintigraphy, although technetium-99m compositions are often preferred for such applications. It may be desirable for such applications to have the disposal of a liquid radiodiagnostic. For this purpose liquid eluents may be used, for example, a 5% glucose solution, to elute krypton-81m from the parent nuclide, i.c. rubidium-81 ($^{81}$Rb), provided on a carrier.

A device in which a radioactive daughter nuclide is formed by radioactive decay of a parent nuclide and can then be eluted is termed a radonuclide generator. Various generators are known for generating radiodiagnostics comprising gaseous radionuclides, in particular krypton-81m. Such generators should be suitable for elution with air or oxygen, after which the gas enriched with krypton-81m must be inhaled immediately by the patient in connection with the short half life of the radionuclide. By situating suitable detection apparatus, for example, a gamma camera, near the patient during said inhalation, a study can be made of, for example, the patient's lung function. In the systems most in use the parent nuclide is provided on an adsorption agent in a column in which during the elution the gaseous eluent is allowed to flow through the column. As adsorption agents for the column are to be considered ion exchanging resin beads and zirconium phosphate, for example, as indicated in publications of Mostafa et al (J. Nucl. Med. 24, 157–159, 1983) and of Beyer et al (Int.J.Appl-.Radiat.Isot. 35, 1075–1076, 1984). During the elution the gaseous daughter nuclide, i.c. krypton-81m, is entrained by the gas flow while the parent nuclide, i.c. rubidium-81, must remain behind on the column. However, as a result of the presence of a pressure drop over the packed column, the elution efficiency is detrimentally influenced and in certain circumstances may even be some tens of percents lower than the maximally achievable yield. An improvement can be achieved by using a humidifying system to humidify the gaseous eluent prior to elution; also in the system described by Mostafa et al a humidifier is used. Apart from the fact that an elution efficiency which is satisfactory in every respect is not yet achieved by humidifying the air or oxygen, other disadvantages are introduced by the use of a humidifier: the system becomes more complicated and the purity (asepsis) of the air or oxygen to be used for elution may be compromised. The elution efficiency can be considerably improved by causing the gaseous eluent to flow through the adsorption column at a lower rate. However, the residence time of the eluate, i.e. of the air or oxygen enriched with radionuclide, in the supply lines to the patient then increases, as a result of which the loss of radionuclide due to radioactive decay also increases.

In the above publication of Beyer et al a new type of $^{81}$Rb-$^{81m}$Kr generator is introduced in which a certain type of foil in which the parent nuclide has been provided is used instead of a column loaded with rubidium-81. The attempt of providing the parent nuclide in the foil in a simple manner has obviously not been successful. A system suitable for elution can be obtained only by implanting rubidium-81 ions into the plastic foil by means of an accelerator. It will be obvious that such a system is highly impractical and is to be considered to be of a theoretical interest only.

In order to avoid the above problems which are associated with the pressure drop over the packed column, a so-called paper generator has been developed: Nucl-.Instr. Methods 156(1978), 369–373. In this generator winded filter paper is used as a carrier for the parent nuclide and is accommodated in a cylinder. The operation of the generator is based upon the absorption of a rubidium-81-containing aqueous solution by the filter paper and on the diffusion of the desired daughter nuclide krypton-81m to the passing air or oxygen used as an eluent. This system is less universal than the system using a packed column because in the first-mentioned system liquid cannot be used as an eluent in practice. Moreover, the parent nuclide in the described paper generator is much more weakly bound to the carrier, which increases the risk of the presence of traces of rubidium-81 in the radiodiagnostic ($^{81}$Rb breakthrough).

It is the object of the invention to provide a method of preparing a radiodiagnostic comprising a gaseous radionuclide in which the above disadvantages do not occur. According to the present invention this object can be achieved by using in the method described in the opening paragraph, in which the radioactive daughter nuclide, in particular krypton-81m, is eluted with a suitable eluent from the parent nuclide, in particular rubidium-81, provided ionically on a carrier, as a carrier for the parent nuclide ions a membrane, in particular an ion exchange membrane, past which the eluent is made to flow.

It has been found that when such a membrane is used as a carrier for the parent nuclide, the disadvantages of the use of a packed column as a carrier are avoided, while nevertheless the good properties of such a column are maintained. In this manner the system according to the invention is pressureless because during the elution the eluent may be caused to flow past the membrane. In this manner an elution efficiency can be reached which is considerably higher and less influenced by the elution rate than when a packed column is used; this will be illustrated in greater detail in the examples. Furthermore, when air or oxygen is used as an eluent, humidifying hereof has become superfluous. The rigid bond of the parent nuclide ions in the membrane matrix reduces the possibility of a breakthrough of undesired nuclides compared with the paper generator described hereinbefore. Finally, the method according to the invention is universally applicable because both gaseous eluents, like air or oxygen, and liquid eluents, like a glucose solution or another suitable eluting liquid, may be used in the elution.

It has been found surprisingly that an equally high elution efficiency is obtained by making the eluent to flow past one side of the membrane on which the parent nuclide has been provided, instead of past both sides. The great advantage hereof is that in this manner the generator may have a simpler construction, as will be described hereinafter, while also the possibility of a breakthrough into the eluent and of a contamination of the eluent with the parent nuclide is reduced.

The invention also relates to a method of preparing a radiodiagnostic comprising a gaseous radionuclide, which method comprises in addition to the elution process the loading process in which, prior to the elution, the membrane to be used according to the invention is loaded with parent nuclide by causing a solution of parent nuclide ions to pass through the membrane; the parent nuclide remains behind in the membrane matrix. Compared with a granular adsorption agent in a column, a membrane can better be handled, so that the manipulations which are necessary for the loading operation can be carried out more easily.

The method of preparing the radiodiagnostic is preferably carried out in such manner that the membrane is loaded by causing the ion solution to pass through the membrane via successively upper surface and lower surface, and that the elution is carried out afterwards by making the eluent to flow past the lower surface of the membrane. In this manner it is ensured that a breakthrough of parent nuclide does not occur. In other words, by carrying out the loading and the elution in this manner, parent nuclide is not found in the eluate, i.e. in the resulting radiodiagnostic, irrespective of the rate at which the elution is carried out. In addition, in this manner optimum use is made of a second property of the membrane: the filtering activity. Should any undesired particles ("particulate matter"), like dust particles, arrive on the membrane during the loading operation, than these particles can never reach the eluate in this manner.

The invention further relates to a radionuclide generator, suitable for using the above method of preparing a radiodiagnostic comprising a gaseous radionuclide, According to the invention the radionuclide generator is characterised in that the generator comprises a membrane, optionally supported by a grid, in particular an ion exchange membrane, which is accommodated in a room enclosed by a generator housing having inlet and outlet apertures in such a manner that an eluent can be made to flow through the room past the membrane. The small size of the membrane enables an extremely compact construction of the generator. As a result of this the lead shielding jacket may be kept small and hence comparatively light. This facilitates transport, which means a great advantage with respect to the logistic problems which frequently occur with shortliving radioactive material. Moreover, the handling of the generator in the clinic is facilitated by the low weight. In addition, the extremely small size enables the administration of a highly-active bolus, for example, a krypton-81m bolus, in a very small volume, so that the possibilities for using the generator are expanded. The grid optionally to be used for supporting the membrane is preferably manufactured from a radiation-resistant and rigid material, for example, stainless steel or chromium-plated nickel. The positioning of the membrane in the room should be adapted to the inlet and outlet apertures for the eluent in such a manner that during the elution said eluent can readily be made to flow past the membrane.

In a practical embodiment the radionuclide generator is constructed in such a manner that the membrane is circumferentially sealingly attached in the generator housing and so divides the room into two parts, one part of said room comprising an inlet aperture in the generator housing for the solution to be used for loading the membrane, the other part of the room comprising an outlet aperture for the loading solution. These provisions permit of loading the membrane with parent nuclide in the room itself, so inside the generator housing. For this purpose the loading solution, i.e. the solution of the parent nuclide ions, is provided through the inlet aperture of the generator housing into the room, is pumped or sucked through the membrane and discharged on the other side of the membrane through the outlet aperture. The generator then is ready for use, that is to say, ready for elution. If desired, the resulting generator can be sterilised in a very simple manner, for example, by autoclaving.

In a certain embodiment which will be described in greater detail hereinafter the radionuclide generator according to the invention is constructed in such a manner that, in addition to the inlet and outlet apertures, the generator housing comprises a closable by-pass which interconnects the parts of the room. Upon loading the membrane the by-pass is closed so that the loading solution must pass through the membrane. During elution the by-pass is opened so that the eluent is made to flow past the membrane via inlet aperture, by-pass and outlet aperture. A correct positioning of the membrane with respect to the apertures in the generator housing and of the bypass favours an optimum elution.

In a preferred embodiment which differs from the embodiment described hereinbefore the radionuclide generator according to the invention is constructed in such a manner that said one part of the room comprises the said inlet aperture in the generator housing intended for the loading solution and the other part, which is separated from said first part by the membrane, comprises an outlet aperture intended for the eluent, which aperture is positioned in the generator housing approximately oppositely to the outlet aperture for the loading solution. Said latter aperture also serves as an inlet aperture for the eluent (bifunctional aperture). Structurally this construction is simpler than the construction of the generator described hereinbefore, while in addition the filtering properties of the membrane are used; this will be described in greater detail hereinafter. Another advantage presented by this embodiment is the possibility of allowing the outlet apertures of loading solution and eluent not to coincide. As a result of this, the outlet aperture for the eluent is not "contaminated" with parent nuclide during the loading operation, which further reduces the risk of the presence of parent nuclide in the eluate. Moreover, this embodiment presents the possibility of positioning the apertures in the generator housing in such a manner that the loading process is facilitated and the elution is optimised.

It has further proved of advantage to dimension the radionuclide generator in the last preferred embodiment so that the membrane divides the room in such a manner that the volume of the one part, provided with said inlet aperture for the loading solution, is small with respect to the volume of the other part provided with the outlet aperture for the eluent and the bifunctional aperture. By minimising the volume of the first-mentioned room, i.e. making it as small as possible, the elution efficiency can still be further improved.

BRIEF DESCRIPTION OF THE DRAWINGS

The invention will now be described in greater detail hereinafter with reference to the ensuing specific examples and illustrated with reference to the accompanying drawings. In these drawings.

Figure 1:
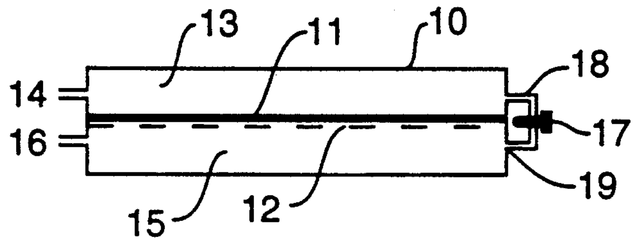
FIGS. 1 and 2 are diagrammatic longitudinal sectional views of two different embodiments of radionuclide generators according to the invention.

The radionuclide generator shown in the longitudinal sectional view of FIG. 1 comprises a membrane 11 which is circumferentially sealingly attached in the generator housing 10 and which is supported by a metal (chromiumplated nickel or stainless steel) grid 12. A Bio-Rex® cation exchange membrane is used as a membrane. The membrane divides the room enclosed by the generator housing into two parts, one part 13 provided with an inlet aperture 14 for the loading solution and the other part 15 provided with an outlet aperture 16 for said loading solution. The generator shown further comprises bypass 18 which can be closed (at 17) and which interconnects the parts 13 and 15. Upon loading the generator with parent nuclide rubidium-81, a solution of rubidium-81 ions $(^{81}Rb^{30})$ is introduced at aperture 14, pumped through the membrane and drained at outlet aperture 16, while the bypass is closed at 17. During elution of the loaded generator the bypass is opened at 17, after which air is made to flow past the membrane as an eluent via aperture 14, bypass 18 and aperture 16. In another experiment described in Example II the elution is carried out in such a manner that the bypass is uncoupled at 19 and the generator housing is closed at 4 and 17, after which the air is made to flow past the membrane via the apertures 19 and 16.

Figure 2:
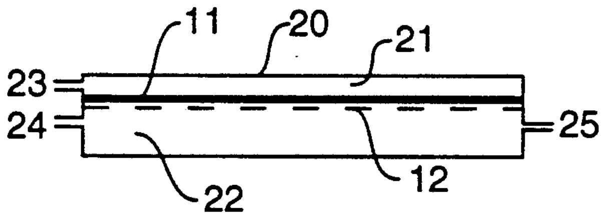

The radionuclide generator shown in the longitudinal sectional view in FIG. 2 has the following internal dimensions: approx. 20 mm×approx. 15 mm×approx. 1 mm. The generator comprises the same membrane 11 which is attached in the housing 20 and is supported by a grid 12 and which divides the room within the housing into two parts 21 and 22, one part (21) of which has a minimum volume. Part 21 comprises an inlet aperture 23 for the loading solution, part 22 comprises an outlet aperture 24 for the eluent and a bifunctional aperture 25 which upon loading serves for draining the loading solution and during elution serves for introducing the eluent. Upon loading the FIG. 2 generator with rubidium-81 as a parent nuclide the solution comprising the parent nuclide ions is introduced at aperture 23 and pumped through the membrane. Since aperture 24 is closed, the solution leaves the generator via aperture 25. During the elution the aperture 23 is closed, after which the elution is carried out with air via apertures 25 and 24.

EXAMPLE I Elution of the generator shown in FIG. 1 via 14–18–16

Figure 3:
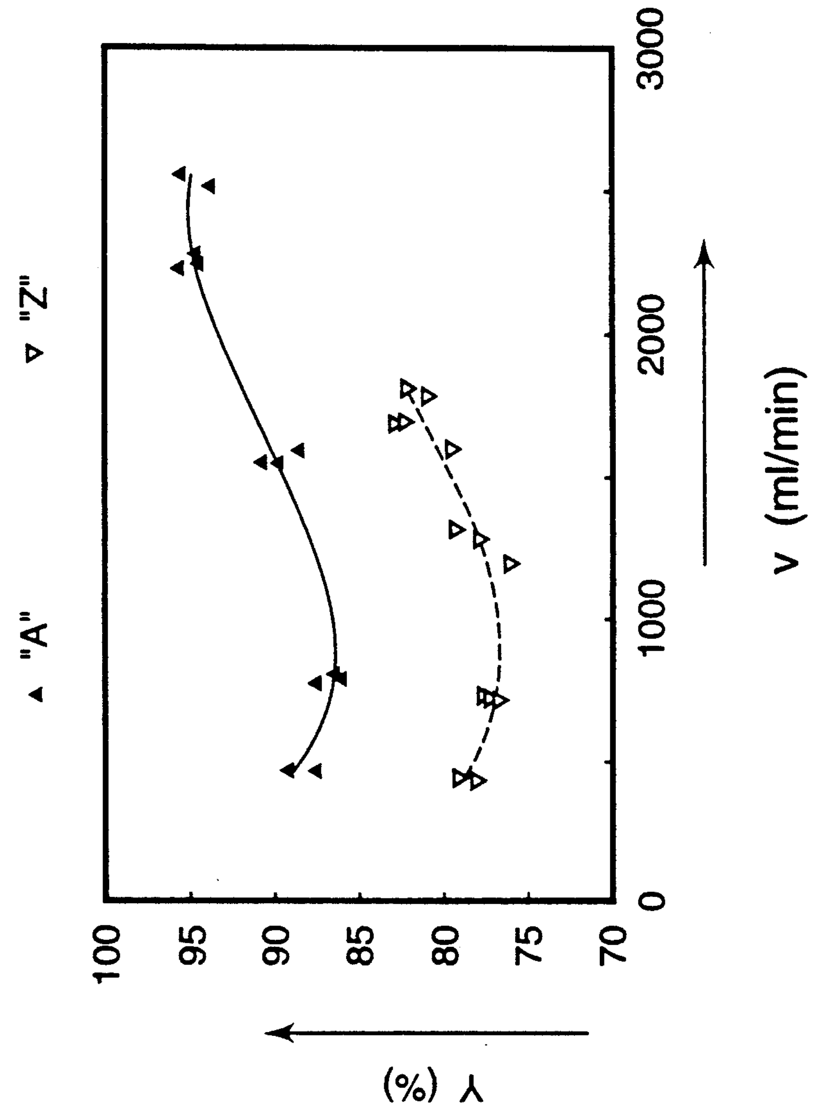
FIGS. 3, 4 and 5 are graphs showing the elution efficiencies of the generators shown; these Figures will be described with reference to the specific examples.

The generator shown in FIG. 1 is eluted via inlet aperture 14, bypass 18 and outlet aperture 16 using air as an eluent. The krypton-81m activity is measured at different flow rates of the air in an arrangement conventionally used for this purpose and consisting of a Ge/Li detector coupled to a multichannel analyser. Comparison is made with a known generator having an adsorption column packed with an ion exchange resin (Dowex® 50 W-X8; 100–200 mesh). For measuring the flow rate a flowmeter is connected at the end of the system. Both generators, the generator shown in FIG. 1 and the known generator, are loaded with rubidium-81 from the same loading solution and with the same loading system. Because the known generator has to be eluted with moist air to obtain reproducible values, the generator according to the invention is also eluted with the same moist air; this is not necessary but it enables a better comparison of the results. All the radioactivity measurements have been corrected for radioactive decay. The results are recorded in the graphs of FIG. 3. In the graphs the elution efficiency Y (% yield in the measuring position) is plotted against the flow rate v of the air flow in ml/min. From the obtained curves it appears that the yield of krypton-81m when using the generator "A" according to the invention as shown in FIG. 1 is 10 to 15% higher than when using the known generator "Z". Moreover, a much higher flow rate can be achieved.

EXAMPLE II Elution of the generator shown in FIG. 1 via 19–16

Figure 4:
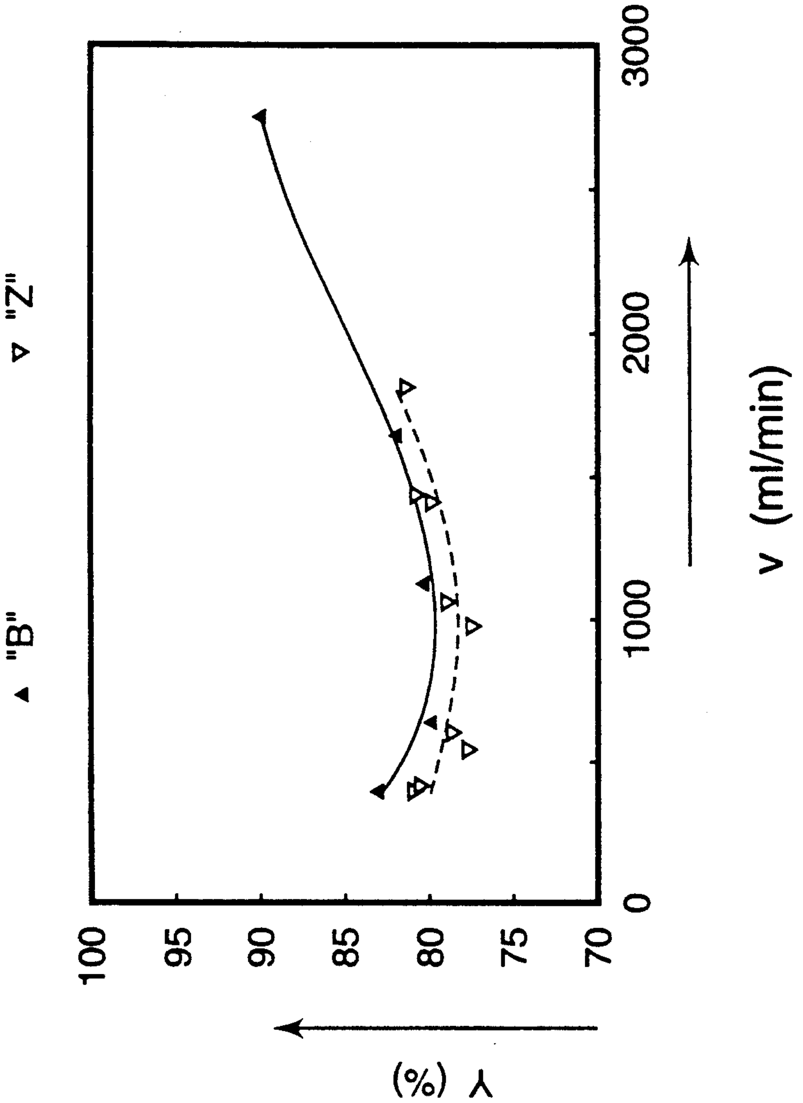

After uncoupling the bypass 18, the air flow is now introduced into the generator at 19, is made to flow past one side of the membrane and is then exhausted from the generator at 16. Whereas in the experiments described in Example I a slight breakthrough of $^{81}Rb$ is observed occasionally, the eluate, i.e. the air enriched with krypton-81m, is now entirely free from parent nuclide contamination. The experiments are otherwise carried out as described in Example I. The results are recorded in the graphs of FIG. 4, again in comparison with the known generator having a packed column. The elution efficiency Y for the generator according to the invention "B" is surprisingly high, even higher than upon elution with the known generator "Z".

EXAMPLE III Elution of the generator shown in FIG. 2 via 25–24

Figure 5:
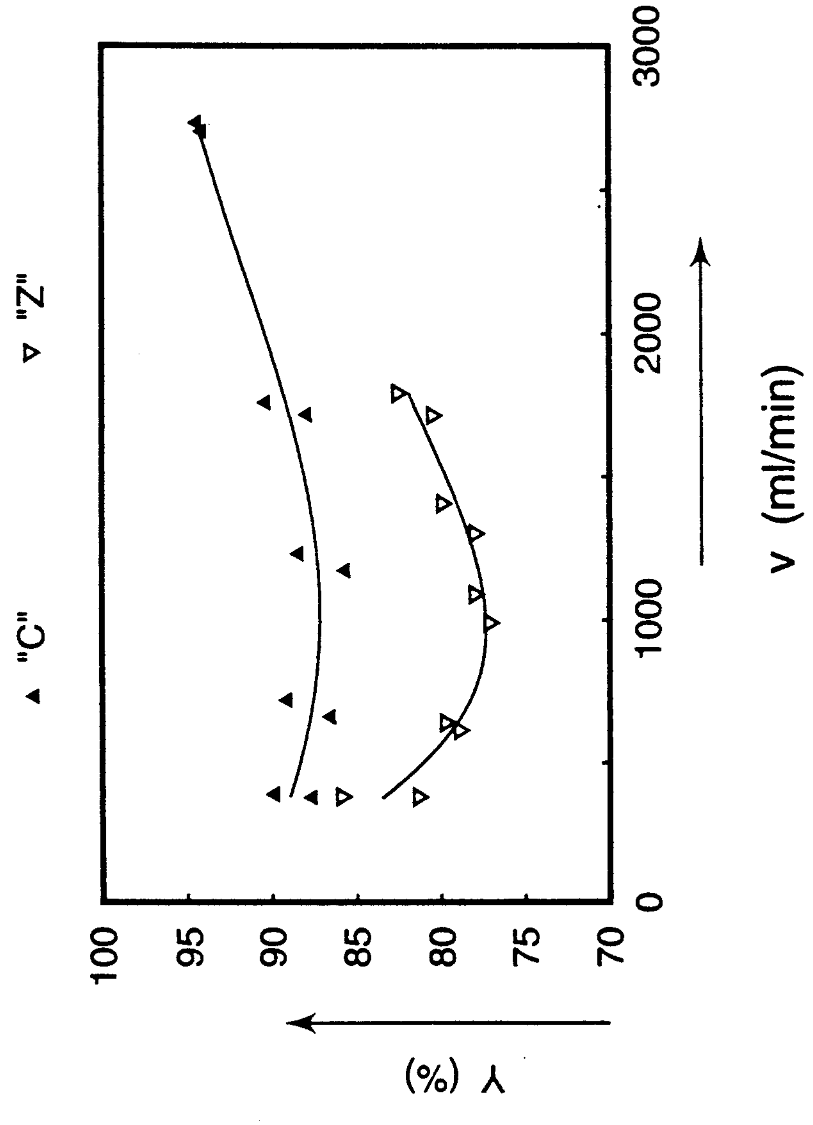

The generator shown in FIG. 2 is eluted with air via 25–24. The eluate is entirely free from parent nuclide, while, as appears from the graphic results shown in FIG. 5, the elution efficiency Y equals the efficiency obtained according to example I. The difference in efficiency between the generator according to the invention "C" shown in FIG. 2 and the known generator "Z" having a packed column is remarkable.

We claim:

1. A method or preparing a radiodiagnostic including a gaseous radioactive daughter nuclide formed by radioactive decay of a parent nuclide, the method comprising the step of eluting, with an eluent, the radioactive daughter nuclide from the parent nuclide, the parent nuclide being provided ionically on an ion exchange membrane, past which the eluent is made to flow.

2. A method as claimed in claim 1 of preparing a radiodiagnostic including krypton-81m formed by radioactive decay of rubidium-81, the method comprising the step of eluting said radionuclide from the rubidium-81, the rubidium-81 being provided ionically on an ion exchange membrane, past which the eluent is made to flow.

3. A method as claimed in claim 1, characterized in that the elution is carried out by causing the eluent to flow past one side of the membrane on which the parent nuclide has been provided.

4. A method as claimed in claim 2, characterized in that the elution is carried out by causing the eluent to flow past one side of the membrane on which the parent nuclide has been provided.

5. A method as claimed in any of the claims 1–4, characterized in that, prior to the elution, the membrane is loaded with parent nuclide by passing a solution of parent nuclide ions through the membrane, the parent nuclide remaining behind in the membrane matrix.

6. A method as claimed in claim 5, characterized in that the membrane is by causing the ion solution to pass through via successively an upper membrane surface and a lower membrane surface and that afterwards the elution is carried out by making the eluent to flow past the lower membrane surface.

7. A radionuclide generator suitable for using the method as claimed in claim 1, characterized in that the generator comprises an ion exchange membrane, optionally supported by a grid, which is accommodated in a room enclosed by a generator housing comprising inlet and outlet apertures, in such a manner that an eluent can be made to flow through the room past the membrane.

8. A generator as claimed in claim 7, characterized in that the membrane is circumferentially sealingly attached in the generator housing and in this manner divides the room into two parts, one part of said room comprising an inlet aperture in the generator housing for the solution to be used for loading the membrane, the other part of the room comprising an outlet aperture for the loading solution.

9. A generator as claimed in claim 8, characterized in that, in addition to the inlet and outlet apertures, the generator housing comprises a closable by-pass which interconnects the parts of the room.

10. A generator as claimed in claim 8, characterized in that said one part of the room comprises the inlet aperture in the generator housing intended for the loading solution and the other part, which is separated from said first part by the membrane, comprises an outlet aperture intended for the eluent, said outlet aperture being positioned in the generator housing approximately oppositely to the outlet aperture for the loading solution, said latter aperture equally serving as an inlet aperture for the eluent such that the aperture is bifunctional.

11. A generator as claimed in claim 10, characterized in that the membrane divides the room in such a manner that the volume of the one part provided with said inlet aperture for the loading solution is small with respect to the volume of the other part provided with the outlet aperture for the eluent and the bifunctional aperture.

* * * * *